(12) United States Patent
Koehler et al.

(10) Patent No.: US 10,207,060 B2
(45) Date of Patent: Feb. 19, 2019

(54) THERAPY APPLIANCE

(75) Inventors: Ulrich Koehler, Marburg (DE); Volker Gross, Wettenberg (DE); Keywan Ali Sohrabi, Glessen (DE)

(73) Assignee: NLI GMBH, Marburg (DE)

( * ) Notice: Subject to any disclaimer, the term of this patent is extended or adjusted under 35 U.S.C. 154(b) by 457 days.

(21) Appl. No.: 13/993,577

(22) PCT Filed: Nov. 21, 2011

(86) PCT No.: PCT/EP2011/005849
§ 371 (c)(1),
(2), (4) Date: Aug. 12, 2013

(87) PCT Pub. No.: WO2012/079684
PCT Pub. Date: Jun. 21, 2012

(65) Prior Publication Data
US 2014/0290646 A1 Oct. 2, 2014

(30) Foreign Application Priority Data
Dec. 13, 2010 (DE) .......... 10 2010 054 361

(51) Int. Cl.
A61M 11/00 (2006.01)
A61M 11/02 (2006.01)
(Continued)

(52) U.S. Cl.
CPC ...... *A61M 11/001* (2014.02); *A61M 15/0003* (2014.02); *A61M 15/009* (2013.01);
(Continued)

(58) Field of Classification Search
CPC .............. A61M 11/001; A61M 15/009; A61M 15/0003; A61M 16/0069; A61M 16/06; A61M 2016/0036; A61M 16/0875; A61M 2016/0027; A61M 2016/0021; A61M 2230/62; A61M 15/08; A61M 11/02

USPC ............ 128/200.12, 200.14, 200.16, 200.19, 128/200.21, 200.22, 200.23, 203.12, 128/203.14, 203.15, 203.21
See application file for complete search history.

(56) References Cited

U.S. PATENT DOCUMENTS 6,705,316 B2 * 3/2004 Blythe .............. A61M 15/0065
128/200.18
2004/0210153 A1 10/2004 Tsukashima et al.
(Continued)

FOREIGN PATENT DOCUMENTS

DE 102008050218 7/2009
EP 2 085 105 8/2009
WO WO 2006/102345 9/2006

OTHER PUBLICATIONS

International Search Report issued by the European Patent Office in International Application PCT/EP2011/005849 dated Mar. 9, 2012.
(Continued)

*Primary Examiner* — Peter S Vasat
(74) *Attorney, Agent, or Firm* — Henry M. Feiereisen LLC

(57) ABSTRACT

A therapy appliance, in particular for use for administering medicaments by nasal inhalation, includes a ventilation tube, on the input side of which is attached an aerosol generator connected to a medicament container, which aerosol generator is connected to a control unit. The ventilation tube is attached at the end to a nasal applicator.

10 Claims, 2 Drawing Sheets

(51) Int. Cl.
*A61M 15/00* (2006.01)
*A61M 16/00* (2006.01)
*A61M 16/06* (2006.01)
*A61M 15/08* (2006.01)
*A61M 16/08* (2006.01)

(52) U.S. Cl.
CPC ........ *A61M 16/0069* (2014.02); *A61M 16/06* (2013.01); *A61M 11/02* (2013.01); *A61M 15/002* (2014.02); *A61M 15/08* (2013.01); *A61M 16/0875* (2013.01); *A61M 2016/0021* (2013.01); *A61M 2016/0027* (2013.01); *A61M 2016/0036* (2013.01); *A61M 2230/62* (2013.01)

(56) References Cited

U.S. PATENT DOCUMENTS

| | | | |
|---|---|---|---|
| 2005/0217666 A1* | 10/2005 | Fink | A61K 31/7036 128/200.14 |
| 2005/0229927 A1* | 10/2005 | Fink | A61M 11/005 128/203.12 |
| 2005/0268916 A1 | 12/2005 | Mumford et al. | |
| 2007/0208269 A1* | 9/2007 | Mumford | A61B 5/0002 600/546 |
| 2008/0029093 A1* | 2/2008 | Stenzler | A61K 33/00 128/203.25 |
| 2008/0257337 A1* | 10/2008 | Denyer | A61M 11/005 128/200.14 |
| 2010/0074881 A1 | 3/2010 | Boucher et al. | |
| 2010/0137828 A1* | 6/2010 | Michard | A61M 5/1723 604/503 |
| 2013/0000641 A1* | 1/2013 | Mazela | A61M 16/0816 128/203.29 |

OTHER PUBLICATIONS

David E. Geller et al. :"The I-neb Adaptive Aerosol Delivery System Enhances Delivery of α1-Antitrypsin with Controlled Inhalation", vol. 23, Supplement 1, Apr. 2010. DOI: 10.1089/jamp.2009.0793.

* cited by examiner

THERAPY APPLIANCE

CROSS-REFERENCES TO RELATED APPLICATIONS

This application is the U.S. National Stage of International Application No. PCT/EP2011/005849, filed Nov. 21, 2011, which designated the United States and has been published as International Publication No. WO 2012/079684 A1 and which claims the priority of German Patent Application, Serial No. 10 2010 054 361.6, filed Dec. 13, 2010, pursuant to 35 U.S.C. 119(a)-(d).

BACKGROUND OF THE INVENTION

The invention relates to a therapy appliance, in particular for an individualized nasal longtime inhalation therapy with a ventilation tube to an inlet side of which an aerosol generator is connected, which aerosol generator is connected with a medicament container.

The prevalence of chronic pulmonary diseases such as bronchial asthma or chronic obstructive pulmonary diseases (COPD) in the adult population in Germany is estimated to be 10 to 15%. Globally, these diseases are the fourth most common cause of death. For the next decades a further increase of these chronic pulmonary diseases is to be expected. According to the WHO, by the year 2020 COPD will advance to rank third among the most common causes of death.

Inhalation therapy plays a central role in many patients with cystic fibrosis, bronchial asthma and COPD. Inhalational administration of steroids, anti-cholinergics and β-symphathomimetics allows reducing side effects compared to oral administration and achieving better therapy success.

Many patients perform one or multiple inhalations daily, which however due to incorrect application have no or only a diminished effect. At the same time, sometimes multiple doses are inhaled, which often results in overdosing and can lead to a higher mortality, particularly in patients with existing cardiovascular conditions.

DE 10 2008 050 218 describes a system and a method for administering inhalable substances into a lung, in particular into an animal lung, which is connected to a respirator. During the development phase of a new active substance, the active substance is normally only available in small amounts, thus making efficient application during the testing phase particularly important. This system is thus used as testing system and testing method during the development phase of new active substances.

An apparatus and a method for optimizing a dose deposition in inhalational medicament application is described in EP 2 085 105. The apparatus first determines the individual breathing volume of a patient in order to optimize the intended deposition of the medicament dose in a predetermined region of the lung. For this, the medicament-particle-concentration in a medicament-aerosol-amount is adjusted to the determined breathing volume and inhaled via a mouthpiece. A detection device signals the reaching of the breathing volume of the medicament-aerosol-amount required for deposition of the intended medicament dose in the predetermined region of the lung with one breath.

In COPD, pathophysiological inflammatory changes of the small airways lead to their obstruction. As a result, the desired therapeutic effect can only be achieved to a limited degree with conventional medicinal inhalation methods. Problematic in the previous therapy of the disease is that the obstruction prevents conventional medicaments (betamimetics, steroids) from reaching the peripheral airways. Further, symptoms occur more frequently at night (Hypoventilation, chrono-biological rhythm).

Patients may more readily comply with and accept the aerosol therapy if the time of the therapy could be shifted from an active process during the day to a passive process during the night.

SUMMARY OF THE INVENTION

The invention is based on the object to provide a therapy appliance of the above-mentioned type, which enables a particularly targeted and controlled application or administration of medicaments into the airways, in particular into the lung of a patient.

According to the invention, this object is solved in that a ventilation tube is connected at its end-side to a nasal applicator.

Advantageous embodiments of the invention are the subject matter of the sub-claims.

The invention is based on the idea that a particularly targeted and controlled application or administration of medicaments into the airways of the patient can in particular be achieved by consequently basing the medication on nasal-inhalation, thereby taking advantage of the comparatively slow air or gas exchange processes that can be achieved therewith. In contrast, in patients with poor pulmonary functional parameters (for example in the case of hard to adjust bronchial asthma), inhalation therapy often can no longer be successfully applied using conventional methods. However, a controlled, pressure-supported, nocturnal application of an aerosol agent via the nose allows optimizing this therapy.

The new device also allows pursuing new therapy approaches. For this, an individualized longtime inhalation therapy with an individual dose at individual time profile is used. This device enables administration of different medicaments in defined concentrations at defined time points. This concept can be used for example for combination treatment with steroids and betamimetics in patients with COPD. The method leads to a more efficient use of agents and at the same time less side effects. The slow release of agents over a longer period of time (Low Dose-Long-Term) has proven very advantageous because for many agents, a constant level of the agent in the blood plasma is desirable. With the new device and the new method, such a low dose-long time inhalation therapy can be performed.

The effect of the nasal inhalation is additionally improved by a controlled ventilation.

Specific delivery of a bolus in the breathing cycle allows differentiating with regard to the site of action (peripheral/central) depending on whether an aerosol bolus is administered at the beginning or at the end of the inspiration.

The inspiration time during an inhalation can be extended through the controlled ventilation. The long retention times of the particles in the lung facilitate deposition of these particles due to sedimentation and diffusion processes, and increase the transition of the agent into the lung.

Preferably, the artificial extension of the inspiration time during the inhalation is only performed during sleep, in order not to be perceived as unpleasant by the patient. The sleep phases can be detected for example by actigraphy (position sensor) or by analyzing the variability of the heart frequency (pulseoximeter).

In an advantageous embodiment, the aerosol generator is configured as aerosol nebulizer, which generates the aerosol in particular by mixing a previously atomized medicament dose into a gas or airstream. The aerosol nebulizer is preferably configured so as to be capable of producing aerosol particles with a size between 0.1 and 10 µm by selecting the compressor pressure and/or by using defined filters.

In order to administer a nebulized medicament in the form of an aerosol over the nose into the airways and the lung, the aerosol particles first have to pass the nasal tract. However, the nose is a very efficient particle filter, which only allows very small particles to pass into the lung. Choosing an appropriate particle size which as far as possible is in the range between 0.1 and 3 µm (ideally 1.3 µm) ensures that a maximum number of inhaled aerosol particles escape being filtered out by the very efficient filter system of the nose and are thus inhaled into the lung. However, if a deposition in the nasopharynx is desired, this can be realized simply by correspondingly varying the particle size, preferably in this case the particle sizes are between 3 µm and 10 µm.

Preferably, the aerosol generator is connected with the control unit and is activated by the control unit according to a predetermined activation pattern. In an advantageous embodiment, the control unit additionally limits the inhalation flow during the aerosol particle supply in particular to 500 ml/s. In an additional or alternative advantageous embodiment, the control unit regulates the inhalation volume advantageously to more than 0.3 l. The thus preferably comparatively low inspiration flows as noted above contribute to avoiding a high nasal deposition. The inhalation volume on the other hand causes a high efficiency of the aerosol application in the lung.

Due to the nocturnal spontaneous breathing, the inhalation speed is rather low, which is advantageous for the deposition in the pulmonary periphery. In addition, particularly advantageously in ventilated patients, the inhalation flow is adjusted correspondingly low during the aerosol application phases or/and is ensured by appropriate selection of mechanical flow limiters.

The control device activates the aerosol generator, advantageously adjusted to the breathing pattern of the patient, according to an activation pattern of periodical, integer multiples of the breathing pattern tact of the patient. Preferably, the control device generates an aerosol bolus every third, fifth, seventh or eighth breath.

According to a preferred embodiment, the control unit activates the aerosol generator during the breathing out or exhaling of the patient for generating an aerosol bolus into the breathing tube. This means, that the ventilation tube serves as aerosol reservoir and during breathing out of the patient (which advantageously occurs in the manner of a multi-strand system in a separate tube and bypassing the ventilation tube) is filled anew to be breathed empty during the subsequent inhalation.

The ventilation tube thus serves the function of an application aid, of a so-called spacer. The aerosol particles are homogenously mixed in the spacer and kept afloat. In addition, the spacer facilitates the slow breathing-in of the aerosol particles. Through the targeted combination of particle size, inhalation flow and inhalation volume, the therapy appliance makes it possible, to significantly lower the negative effect of the particle filter function of the nose and at the same time to increase the efficiency of the particle deposition into the lung.

In an advantageous embodiment, a respirator device is provided, which continuously supplies breathing air and/or oxygen to the patient via the ventilation tube during the inhalation according to a predetermined breathing pattern. The predetermined breathing pattern of the respirator is preferably adjusted to the oxygen requirement of the patient, which is preferably determined from the pulseoximetry.

Advantageously, a pressure-controlled respirator appliance is used within the framework of this respirator device. The pressure-controlled respirator appliance is advantageously configured as CPAP (Continuous Positive Airway Pressure)—appliance and/or as BIPAP (Biphasic Positive Airway Pressure)—appliance. The noninvasive overpressure-respiration achieves an improved deposition of the aerosol in the lung periphery. The applied overpressure generates a pneumatic bracing of the small airways and thus keeps them open, to enable access to obstructive regions of the peripheral lung such as for example in COPD—patients.

Preferably, this system is equipped with multiple medicament containers and enables releasing an amount of aerosol and generating a time profile that are adjusted to the respective agent, in order to for example administer bronchial dilators and anti-inflammatory agents at different time points and in different amounts.

In an advantageous embodiment, the therapy appliance further has a sensor for determining the position of the patient. In long time inhalation during the night, this allows for example determining whether the patient is asleep, for example because he has not changed his position for a longer period of time. In an advantageous refinement, a corresponding sensor is present for determining the oxygen content of the blood of the patient.

In a preferred embodiment, the nasal applicator is configured as nose mask, which the patient can arrange on his head in a conventional manner. The nasal applicator can also be configured in the form of nasal cannulae.

In an advantageous refinement, a passive flow limiter is provided on the therapy appliance.

Further advantageously, a respiratory flow control in the form of a pneumatograph or spirometer is provided.

In a further advantageous refinement, a detection device is present. In this way, the breathing and the applied amount of aerosol can be monitored and documented. In addition, these data can be integrated in tele-medical concepts. In an advantageous refinement, the adjustment of the aerosol amount can also involve a feedback of defined parameters of the breathing or other parameters (for example when the oxygen saturation is used).

The therapy appliance for controlling nasal aerosol inhalation into the airways, in particular into the lung, of a patient thus essentially includes a respirator device, which is controllable in order to supply the airways of the patient continuously with breathing air via a ventilation tube according to a predetermined breathing pattern. In addition, a regulatable aerosol generator, preferably configured as aerosol nebulizer for supplying aerosol particles into the breathing air stream that flows in the ventilation tube is provided. An also provided control device is configured to activate the aerosol nebulizer according to an activation pattern which is adjusted to the breathing pattern so that a respective aerosol bolus is generated according to periodic integer multiples of the breathing pattern tact.

Particularly advantageously, the invention is used in a method for nasal aerosol inhalation into the airways, in particular into the lungs of the patient, preferably with the following steps:

providing a ventilation tube via which the patient can nasally breathe in and out;

supplying, according to a predetermined activation pattern, aerosol particles by means of an aerosol nebulizer into the air stream that flows in the ventilation tube, wherein the aerosol nebulizer generates aerosol particles with a size of 0.1 to 3 µm, wherein the inhalation flow during the aerosol particle supply is limited to 500 ml/s;

and wherein the inhalation volume during the aerosol particle supply is adjusted to more than 0.3 l.

According to a further aspect, the invention provides a method for nasal aerosol inhalation into the airways, in particular into the lungs of the patient, with the steps:

providing a respirator device which is controllable in order to discontinuously supply breathing air to the airways of the patient via a ventilation tube according to a predetermined breathing pattern;

supplying aerosol particles by means of an aerosol nebulizer into the stream of breathing air that flows in the ventilation tube;

wherein the aerosol nebulizer is activated according to an activation pattern, which is adjusted to the breathing pattern, so that a respective aerosol bolus is generated according to integer multiples of the breathing pattern tact.

The approach according to the invention of the nasal longtime inhalation represents a paradigm shift in the inhalation technology. The active short time inhalation of high dosage during the day is replaced by passive inhalation with low dosages, which can occur during the night over a long period of time. The nocturnal inhalation occurs passively by spontaneous breathing during the sleep for example for 6 to 8 hours. As an alternative, according to the invention an inhalation via a nasal cannula during the wake phase is also possible (this enables a simple application of an aerosol in bedbound patients). Thus, the invention is not necessarily limited to a nocturnal inhalation even though this is preferred.

Previously, inhalation therapy always depended on active cooperation of the patient. The agents were only applied in isolated, strong doses, which increases the risk of deleterious side effects. In addition, pulmonary therapy is not, or only insufficiently achieved with the known inhalation methods. The approach according to the invention is also very well suited for the pediatric field. Especially in order to minimize possible side effects of high doses of the therapeutic agents.

The invention is advantageous because it allows improving dosing and the effect of the medication while at the same time decreasing side effects. Different agents can be applied simultaneously with an individual dose and time profile at a defined site of action. Preferably, bronchial dilators, anti-inflammatory, antibacterial, and mucolytic agents are used.

By means of the nasal inhalation in combination with a noninvasive respiration, a significantly improved deposition of medicaments applied through inhalation can be achieved. The dynamic pressure, which is induced by the noninvasive respiration, is intended to cause a pneumatic opening/bracing of the small airways in order to thus better reach the actual site of action, the pulmonary periphery. In COPD, the small airways are obstructed as a result of the inflammatory changes of the small airways. As a result, the desired therapeutic effect can only be achieved to a limited degree with conventional medicament inhalation methods. Due to the obstruction, common medicaments (betamimetics, steroids) do not reach the peripheral airways. The ailments occur more frequently at night and particularly in the early morning hours. Appropriate feedback in the system (e.g. pulseoximetry) enables an individual response to an obstructive change. Thus, the application of short-time effective betamimetics can for example be increased, in case the oxygen saturation falls below a threshold value. At the same time, the breathing support (for example noninvasive BiPAP) can be increased.

The new technical method for time-controlled regulation of the nasal inhalational application enables an individualized long-time inhalation therapy with an individual dose profile and/or an individual time profile. Different medicaments can be applied in a defined concentration at defined time points and defined individual sites of action.

Preferred embodiments of the invention include combinations of the generated particle size, inhalation flow during the aerosol particle supply and inhalation volume during the aerosol particle supply as set forth in table 1.

Particularly preferred is an embodiment in which the aerosol generator or aerosol nebulizer generates aerosol particles with a size of 1.25 to 1.35 µm, in particular 1.3 µm, and the processor limits the inhalation flow during the aerosol particle supply to 200 ml/s and adjusts the inhalation volume during the aerosol particle supply to 1.5 l.

According to a further preferred embodiment, the aerosol nebulizer is configured so that aerosol particles with a size of 1.25 to 1.35 µm, in particular 1.3 µm are generated and the processor is configured to limit the inhalation flow during the aerosol particle supply to less than 300 ml/s and to adjust the inhalation volume during the aerosol particle supply to 0.5 l.

TABLE 1

|    | Particle size (µm) | Inhalation-flow (ml/s) | Inhalation volume (l) |
|----|--------------------|------------------------|-----------------------|
| 1  | 0.1-3              | <500                   | >0.3                  |
| 2  | 1-2                | <500                   | >0.3                  |
| 3  | 1.25               | <500                   | >0.3                  |
| 4  | 1.30               | <500                   | >0.3                  |
| 5  | 1.35               | <500                   | >0.3                  |
| 6  | 0.1-3              | <300                   | >0.3                  |
| 7  | 1-2                | <300                   | >0.3                  |
| 8  | 1.25               | <300                   | >0.3                  |
| 9  | 1.30               | <300                   | >0.3                  |
| 10 | 1.35               | <300                   | >0.3                  |
| 11 | 0.1-3              | <200                   | >0.3                  |
| 12 | 1-2                | <200                   | >0.3                  |
| 13 | 1.25               | <200                   | >0.3                  |
| 14 | 1.30               | <200                   | >0.3                  |
| 15 | 1.35               | <200                   | >0.3                  |
| 16 | 0.1-3              | <500                   | >0.4-2                |
| 17 | 1-2                | <500                   | >0.4-2                |
| 18 | 1.25               | <500                   | >0.4-2                |
| 19 | 1.30               | <500                   | >0.4-2                |
| 20 | 1.35               | <500                   | >0.4-2                |
| 21 | 0.1-3              | <300                   | >0.4-2                |
| 22 | 1-2                | <300                   | >0.4-2                |
| 23 | 1.25               | <300                   | >0.4-2                |
| 24 | 1.30               | <300                   | >0.4-2                |
| 25 | 1.35               | <300                   | >0.4-2                |
| 26 | 0.1-3              | <200                   | >0.4-2                |
| 27 | 1-2                | <200                   | >0.4-2                |
| 28 | 1.25               | <200                   | 0.4-2                 |
| 29 | 1.30               | <200                   | 0.4-2                 |
| 30 | 1.35               | <200                   | 0.4-2                 |
| 31 | 0.1-3              | <500                   | 1.5                   |
| 32 | 1-2                | <500                   | 1.5                   |
| 33 | 1.25               | <500                   | 1.5                   |
| 34 | 1.30               | <500                   | 1.5                   |
| 35 | 1.35               | <500                   | 1.5                   |
| 36 | 0.1-3              | <300                   | 1.5                   |
| 37 | 1-2                | <300                   | 1.5                   |
| 38 | 1.25               | <300                   | 1.5                   |
| 39 | 1.30               | <300                   | 1.5                   |
| 40 | 1.35               | <300                   | 1.5                   |
| 41 | 0.1-3              | <200                   | 1.5                   |
| 42 | 1-2                | <200                   | 1.5                   |
| 43 | 1.25               | <200                   | 1.5                   |

TABLE 1-continued

| | Particle size (μm) | Inhalation-flow (ml/s) | Inhalation volume (l) |
|---|---|---|---|
| 44 | 1.30 | <200 | 1.5 |
| 45 | 1.35 | <200 | 1.5 |

BRIEF DESCRIPTION OF THE DRAWING

In the following, the invention is explained in more detail with reference to the included drawings. It is shown in.

DETAILED DESCRIPTION OF PREFERRED EMBODIMENTS

Figure 1:
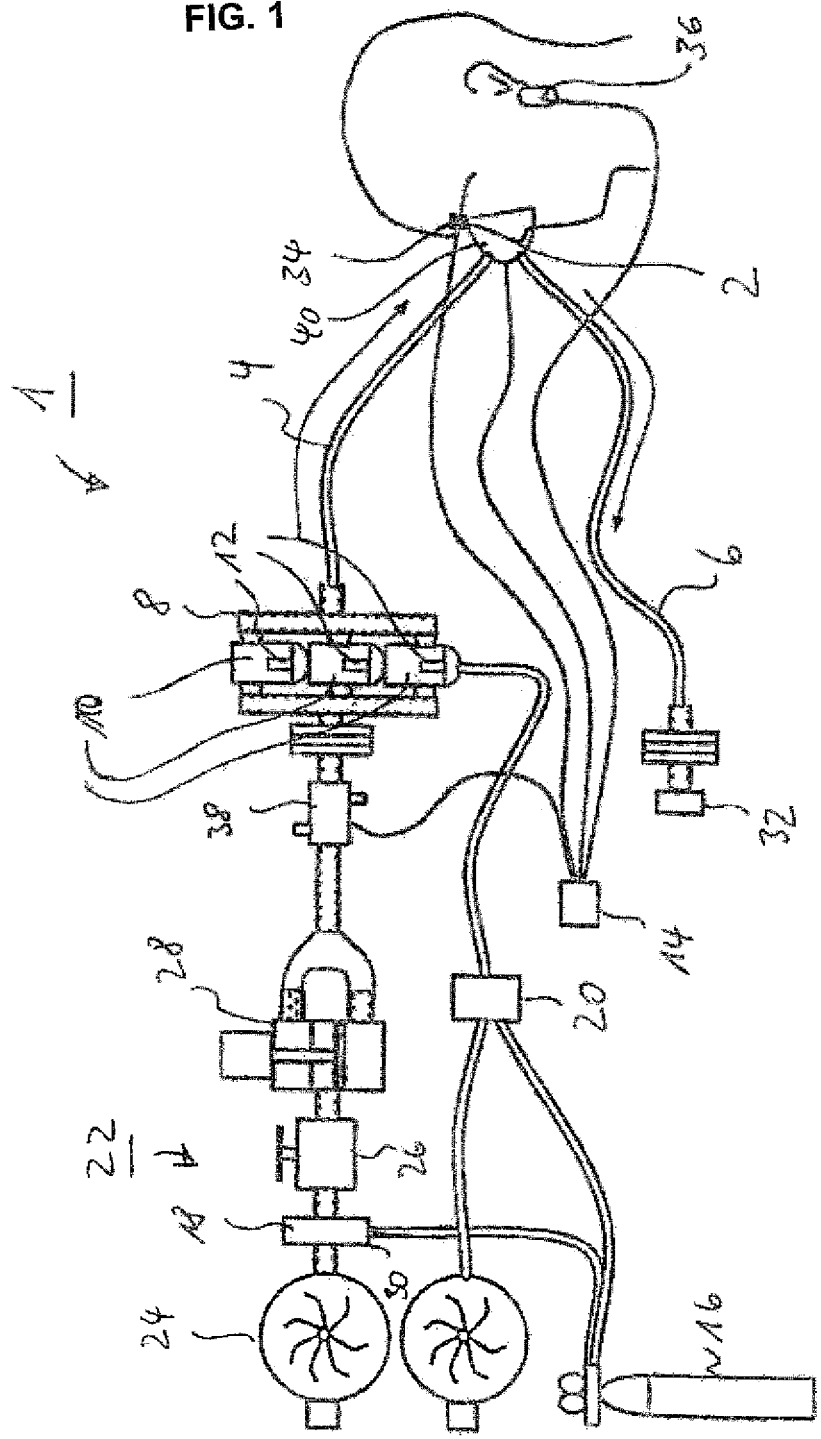
FIG. 1 a therapy appliance in a schematic representation, and
FIG. 2 the achieved lung deposition for two examples in form of a diagram.

FIG. 1 shows a schematic representation of a therapy appliance 1 with a nasal inhalator, which in the exemplary embodiment is configured as breathing- or nose mask 2. Connected to the nose mask 2, which if needed can be provided with a connection piece for example a so-called Y—connector, or a ventilation tube 4—for supplying breathing air charged with medicaments—and a further tube 6, which is connected in parallel to the ventilation tube 4—for enabling exhaling while bypassing the ventilation tube 4. Thus, the ventilation tube 4 functions as a breathing-in tube for inhalation, while the second tube 6 serves as breathing-out tube during the exhalation. Integrated into the nose mask 2 is an appropriate switching valve or inhalation/exhalation valve, here not further shown, which closes or releases the tube inlets depending on the breathing cycle of the patient, so that the patient does not exhale into the ventilation tube or vise versa.

In addition, a not further shown mask-pressure-measuring device for detecting the mask pressure or breathing pressure is provided on the nose mask 2.

On the inlet side of the ventilation tube 4, an aerosol generator 8 is connected. The aerosol generator 8 includes a number of medicament containers 10, in each of which a defined medicament supply can be stored. In particular, different medicaments can be stored in different containers and later be combined with one another depending on the requirement or therapy. Each medicament container 10 is provided with an aerosol nebulizer 12, which produces small amounts of aerosol from the medicaments that are stored in the respective container and feeds them into the breathing air for the patient that is to be supplied into the ventilation tube 4. Instead of a nebulizer, another appropriate aerosol generator can also be provided. In addition, beside the medicament container, a here not shown medicament processor can be provided.

The ventilation tube 4, which connects the aerosol generator 8 with the nose mask 2, is dimensioned, i.e. in particular with regard to its length and it's cross-sectional dimensions, so that the inner volume that is formed by the aerosol generator 8, is capable of performing the function of a so-called spacer. Accordingly, the inner volume is selected so that the breathing air contained therein is sufficiently great, in particular also after being charged with the aerosol, so that an appropriate coordination with the breathing volume of the patient during a breath can be achieved.

The aerosol nebulizers 12, and with this also the aerosol generator 8, together are connected with a common control unit 14. The control unit individually controls the aerosol nebulizers via appropriate signal lines, which for reasons of simplicity are not shown in the figure. This control occurs for each medicament container 10 or each aerosol nebulizer 12 according to a predetermined activation pattern, in order to introduce aerosol particles of a desired size and also of a desired composition or mixture into the ventilation tube 4 according to the breathing—and/or time profile of the patient.

The aerosol nebulizer 12 or each of the aerosol nebulizers 12 is in particular configured so that it generates aerosol particles with a size of 0.1 to 3 μm. The appropriate particle size is generated by using special filters inside the respective aerosol nebulizer 12, here not further shown, or directly via a special aerosol generator, which is also not shown.

In particular, the multitude of medicament containers 10 with the corresponding aerosol nebulizers 12 allows processing and appropriately providing a combination of individual medicaments for the inhalation. In this way, the required medicament can be nebulized via the aerosol nebulizer 12 into the ventilation tube 4 for inhalation as needed and tailored to the patient. In addition, an oxygen reservoir 16 is connected on the side of the inlet to the ventilation tube 4 via a mixer 18 and also to the aerosol generator 8 or individually to all or some of the medicament containers 10 via a distributor valve 20, in order to be able to provide additional oxygen during respiration of the patient and/or during aerosol generation if needed.

In order to be able to actively support the application of the medicaments if and as needed, the therapy appliance 1 also includes a respirator device 22 connected to the entry side on the ventilation tube 4. In the exemplary embodiment, this respirator device 22 is in particular configured as BiPAP system and/or CPAP system and includes a blower 24, a BiPAP valve and/or CPAP valve 26, a so-called resistance valve 28 and a not further shown check valve. The control unit 14, which also controls the aerosol nebulizer 12 or aerosol nebulizers 12, is also connected with these components on a signal side.

During the supply of aerosol particles, the control unit 14 on one hand limits the inhalation flow to 500 ml/s, and on the other hand adjusts the inhalation volume to more than 0.3 l.

The controllable respirator device 22 continuously supplies breathing air to the ventilation tube 4, as the case may be with overpressure, in particular by means of the BiPAP- and/or CPAP-valve 26 according to a predetermined breathing pattern during the inhalation of the patient. The respirator device 22 recognizes the inhalation of the patient and the breathing cycle via appropriate sensors and a corresponding signal analysis and enhances the inhalation of the patient and the breathing cycle in order to ensure a sufficient breathing volume. In order to enable a comprehensive signal analysis and a control of the system components that is appropriate for multiple situations, in particular an oxygen sensor 30, a PEEP-motor 32 (connected to the end of the tube 6), a position sensor 34, a pulseoximeter 36 and sensors 38, 44 for measuring flow/pressure are provided as sensors in the ventilation tube 4.

The breathing pattern to be executed by the respirator device 22 is preferably adapted to the target site of the aerosol deposition in the lung of the patient. The applied overpressure creates a pneumatic bracing of the small airways and in this way keeps the small airways open, to thereby first and foremost enable access into obstructive regions of the peripheral lung.

Figure 2:
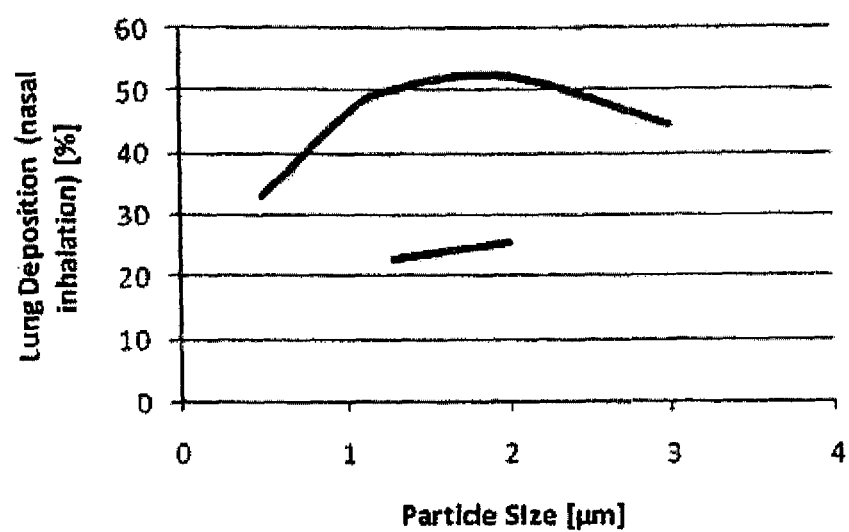

FIG. 2 shows, by way of a preferred embodiment according to the invention, the result of the lung deposition with a therapy appliance 1 for nasal inhalation via a nose mask 2 or nose cannulae. In the here used therapy appliance 1, the regulatable aerosol nebulizer 8 was configured, so that aerosol particles with an average size of 1.3 μm were created. The control device 18 has limited the inhalation flow during the aerosol particle supply to 200 ml/s, and the inhalation volume during the aerosol particle supply was 1.5 l. With this, a lung deposition of 50% of the agent was achieved.

At same particle size, a flow increased to 300 ml/s but reduced to 500 ml, the lung deposition is 25% as also shown in FIG. 2.

What is claimed is:

1. A therapy appliance for administering medicaments to a patient through nasal inhalation, comprising:
    a nasal applicator;
    a ventilation tube having an inlet side and being connected to the nasal applicator on the inlet side;
    medicament containers;
    an aerosol generator, said medicament containers and said aerosol generator being connected to an end-side of the ventilation tube;
    a control unit connected with the aerosol generator, said control unit being constructed to activate the aerosol generator according to an activation pattern, which is adjusted to a breathing pattern of the patient, thereby generating a respective aerosol bolus according to periodical integer multiples higher than 1 of a breathing cycle of the breathing pattern of the patient, wherein a size of aerosol particles of the aerosol bolus is between 0.1 and 3 μm, the control unit further constructed to limit an inhalation flow during supply of aerosol particles generated by the aerosol generator to 500 ml/s and to adjust an inhalation volume to more than 0.3 l; and
    a controllable respiration device constructed for continuously supplying oxygen and/or breathing air according to a predetermined breathing pattern during breathing of the patient, said predetermined breathing pattern being adjusted for targeted deposition of the aerosol in the nasopharynx and/or the lung of the patient.

2. The therapy appliance of claim 1, wherein the control unit is constructed to fill the ventilation tube with the aerosol via the aerosol generator during exhalation of the patient.

3. The therapy appliance of claim 1, wherein the control unit is configured so that a dose of a medication inhaled by the patient follows a time profile that is individually determined for the patient and the medication.

4. The therapy appliance of claim 1, further comprising a sensor for determining a position of the patient.

5. The therapy appliance of claim 1, further comprising a sensor for determining an oxygen content in the blood of the patient.

6. The therapy appliance of claim 1, further comprising a breathing flow control and/or breathing pressure control.

7. The therapy appliance of claim 1, further comprising a data gathering- and/or data transmitting device.

8. A method for nasal aerosol inhalation into the lungs of a patient, comprising:
    controlling a respirator device to continuously supply breathing air to the airways of the patient via a ventilation tube according to a predetermined breathing pattern; and
    supplying aerosol particles with an aerosol nebulizer into a stream of the breathing air flowing in the ventilation tube, wherein the aerosol nebulizer is activated according to an activation pattern, said activation pattern being adjusted to the predetermined breathing pattern, so that a respective aerosol bolus is generated in according to integer multiples higher than 1 of a breathing cycle-of the breathing pattern, wherein a size of aerosol particles of the aerosol bolus is between 0.1 and 3 μm,
    wherein during the supplying of the aerosol particles an inhalation flow is limited to 500 ml/s and an inhalation volume is adjusted to more than 0.3 l, and
    wherein said predetermined breathing pattern is adjusted for targeted deposition of the aerosol in the nasopharynx and/or the lung of the patient.

9. The method of claim 8, wherein the ventilation tube is filled with the aerosol via the aerosol generator during exhalation of the patient.

10. The method of claim 8, wherein a dose of a medication inhaled by the patient follows a time profile that is individually determined for the patient and the medication.

* * * * *